United States Patent [19]
Verhoeven

[11] Patent Number: 5,191,389
[45] Date of Patent: Mar. 2, 1993

[54] DEVICE FOR MEASURING BY HOLOGRAPHY THE DEVIATIONS OF LIGHT RAYS IN TRANSPARENT MEDIA

[75] Inventor: Dean Verhoeven, Rueil-Malmaison, France

[73] Assignee: Institut Francais Du Petrole, Rueil-Malmaison, France

[21] Appl. No.: 606,612

[22] Filed: Oct. 31, 1990

[30]  Foreign Application Priority Data

Nov. 9, 1989 [FR] France .................................. 89 14827

[51] Int. Cl.$^5$ .............................................. G01B 9/21
[52] U.S. Cl. .................................... 356/348; 356/347; 250/237 R
[58] Field of Search ............... 356/347, 348, 239, 129; 250/237

[56]  References Cited
U.S. PATENT DOCUMENTS 3,728,006  4/1973  Brooks et al. ......................... 356/347

Primary Examiner—Samuel A. Turner
Assistant Examiner—LaCharles P. Keesee, II
Attorney, Agent, or Firm—Antonelli, Terry, Stout & Kraus

[57]  ABSTRACT

A process and a device for measuring, through a holographic technique, the deviation of the light rays of a laser beam by more or less transparent objects. The angular deviations (a) of light rays that have passed through the object are measured by an angular measuring instrument (2) located behind an optical system traversed by the light emanating from the object or a hologram formed from the object. The optical system comprises for example one or several lenses (11, 12), the holographic images forming in the object focal plane of the system, and a diaphragm (D3) located in its image focal plane. The measuring can also be carried out, for example, by turning over the obtained hologram of the transparent object and examining it through a diaphragm. The present invention has application, for example, in the study of flames, of liquid or gaseous flows with strong density variations, of turbulent gaseous mixtures in the combustion chambers of engines, etc.

20 Claims, 2 Drawing Sheets

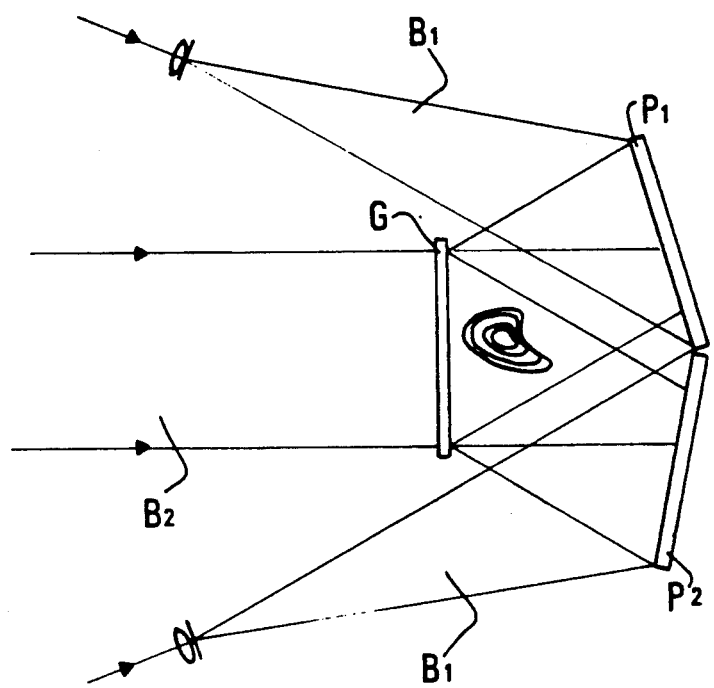

DEVICE FOR MEASURING BY HOLOGRAPHY THE DEVIATIONS OF LIGHT RAYS IN TRANSPARENT MEDIA

BACKGROUND OF THE INVENTION

The present invention relates to a process and a device for measuring through a holographic technique the deviation of light rays in transparent media traversed by a laser beam, and notably of inhomogeneous objects whose refraction coefficient may show strong variation gradients.

The process and the device according to the invention notably apply to the study of the variations of the refraction coefficient of inhomogeneous substances (gaseous, liquid or solid), in order to know some of their properties and notably their composition, their concentration or their temperature. An interesting particular application of the present invention is, for example, the study of turbulent mixtures in the combustion chambers of engines. The study of the properties of transparent objects is generally carried out with optical means by using the property of any transparent object to more or less deviate the light rays traversing it according to variations of its volume and of its refraction coefficient.

There are several well-known deflectometry methods for carrying out these studies. Techniques such as holographic deflectometry, holographic moiré, single-beam deviation measurings or speckle pattern photography can be used. The holographic moiré and the speckle pattern photography techniques are similar insofar as they allow recording of the deviation of the light for a later analysis. Their resolution in time is therefore high. With the moiré technique, only one component, of the deviation of the deviated beam can be measured at a time, and the experimenter must first set the sensitivity and the space resolution. The moiré technique by holography does not have these drawbacks, but the data reduction, that is to say the extracting of the data of interest, is relatively complicated. The technique of speckle pattern photography allows measurement of simultaneously measure the two components of the deviated beam, but a high sensitivity can only be obtained to the detriment of the space resolution, and the values of these two parameters must be set before beginning the measuring. This particular technique is generally utilized for studying objects whose variation gradient of the refraction coefficient is relatively low.

It is also well-known that the moiré or the speckle pattern photography techniques are not applicable when the variations in the refraction coefficient of the examined objects are large enough to cause a crossing of the light rays before their deviation has been measured. The single-beam deviation technique also avoids the drawbacks of the moiré or of the speckle pattern photography techniques. No light ray crossing occurs when it is used, but it is not suitable for the study of transient phenomena.

Applications of these methods known for the study of the variations in the refraction coefficient of transparent objects or media are described in the following publications:

J. Stricker et al, "Holographic Moiré Deflectometry" in Appl. Phys. Lett. Vol. 44 No. 8, 723-725;

U. Koepf, "Applications of Speckling for measuring the deflection of laser light by phase objects" in Opt. Comm. Vol. 5, No. 5, 347-350.

SUMMARY OF THE INVENTION

The process according to the invention avoids many drawbacks of the previous techniques. It allows measuring of the angular deviations undergone by the light of a laser having passed through a more or less transparent object, and notably a gaseous mass, on holograms formed from this object. It is characterized in that the measuring of the angular deviations is carried out by placing an angular measuring instrument behind an optical system traversed by the light emanating from the object or from at least a hologram formed from said object.

The optical system comprises, for example, at least one lens arranged in such a way that part of the reconstructed image of each obtained hologram substantially forms in its object focal plane, and a diaphragm substantially arranged in the image focal plane of the optical system, said angular measuring instrument being located on the other side of the diaphragm in relation to the optical system.

According to the procedure in one embodiment, a recording of each hologram of said object is achieved on a sensitive support, the optical system consisting of a diaphragm arranged in a plane where a part of the real image of each restored hologram forms, this image being obtained by turning over the sensitive support, with the instrument being placed on the side of the diagram opposite the optical system.

According to the procedure in a second embodiment, the optical system comprises at least two lenses arranged in such a way that at least part of the examined object is in its object focal plane, each holographic image being substantially formed in the object focal plane of the optical system.

According to the procedure in another embodiment, each holographic image is recorded on a sensitive support, the measuring instrument being located on the side of the sensitive support opposite the optical system, and each hologram is reconstituted from the recording.

According to a first variant, each holographic image is reconstituted by means of a relatively wide light beam, a diaphragm being interposed between the recording of each hologram and the measuring instrument.

According to a second variant, each holographic image is reconstituted by means of a relatively narrow light beam.

According to another embodiment procedure, several holograms of the examined object can be achieved by lighting it up with several light beams having several different orientations.

The different beams with different orientations are, for example, obtained by means of a diffraction grating.

In the case of multiple beams, the method comprises the successive measuring of the angular deviations of the different beams with different orientations by interposing a space filter in the image focal plane of the optical system.

Whatever the embodiment procedure may be, the angular deviations are advantageously measured by displacing each hologram in relation to the angular measuring instrument.

It is also possible to measure the angular deviations by placing the measuring instrument in the image focal plane of a lens with a relatively long focal distance.

The invention also relates to a holographic deflectometry device for implementing the process. It comprises optical means for forming holograms from the examined objects and an instrument for measuring the angular deviations undergone by light rays after traversing the objects. It is characterized by an optical system interposed in order to direct the light emanating from the object, or from each hologram formed from the object, onto the measuring instrument.

The optical system comprises, for example, at least two lenses associated with a diaphragm. According to an embodiment, the optical system comprises at least one diaphragm.

The measuring instrument comprises, for example, an angle sensor adapted for delivering signals indicating its position in a measuring plane.

The process and the device according to the invention allow an improved control of the crossing of light rays in the study of objects whose refraction coefficient varies with a strong gradient and/or is subject to rapid changes, while giving the possibility of choosing independently from one another the required space resolution and sensitivity. This is possible because:

the space resolution is determined by the aperture of the diaphragm used for forming the scanning beam of the reconstructed hologram, the sensitivity in the measuring of the angular deviations is independent from the space resolution which is defined by the diaphragm aperture, the risk of beams crossing is very low because the diaphragm can be placed right behind the object or even inside it, the practical dynamics of the measuring of angular deviations shown by the method according to the invention are wider than with the interferometric techniques, since the measuring of angular deviations is not more difficult, regardless of whether the deviations are low or high, which is not the case, as it is well-known, when the measurings are carried out by counting the interference fringes, the extracting of useful data can be easily automated when the process according to the invention is applied.

BRIEF DESCRIPTION OF THE DRAWINGS

Other features and advantages of the process and the device according to the invention will be clear from reading the description hereafter of embodiment procedures described by way of non limitative examples, with reference to the accompanying drawings in which:

FIG. 7 also shows very diagrammatically the recording of multidirectional holograms of a transparent object.

DESCRIPTION OF THE PREFERRED EMBODIMENTS

The forming of holograms of an object, and notably of a translucent or transparent object 1 is achieved, as it is well-known, by making two light beams B1 and B2, obtained by dividing a beam emitted by a laser, interfere. One of the beams (B1) serves as a reference beam. The other beam (B2) is directed through the object to be examined. Both beams, suitably collimated by two lenses L1 and L2 (FIG. 1), interfere with one another and form a hologram which can be recorded on a sensitive plate P consisting for example of a photographic plate, a photosensitive thermoplastic plate, etc.

Figure 2:
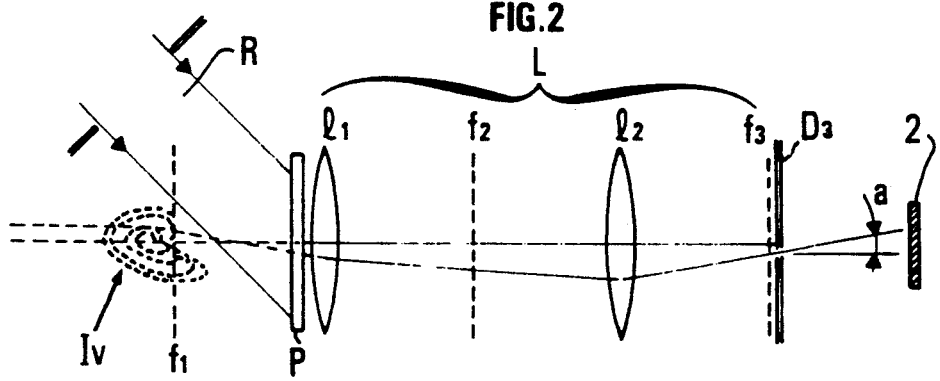
FIG. 2 diagrammatically shows a first embodiment of the equipment where an optical system receives the light coming from a hologram formed from the examined object.

According to the first embodiment of the invention diagrammatically shown in FIG. 2, the image of the recorded hologram is reconstructed by placing the sensitive plate P lit by a reconstruction beam R in such a way that the reconstructed virtual image Iv is in the object focal plane of an optical system L consisting, in the example shown, of a pair of lenses l1, l2. The measurement of the deviations of the light rays is performed by an appropriate measuring instrument 2 which is preferably arranged behind a diaphragm D3 located in the image focal plane of the optical system L. An optical detector of a well-known type that can be displaced within the observation plane and that emits signals indicating the position of the ray passing through diaphragm D3, such as a fine photodiode grating, is preferably used.

Figure 3:
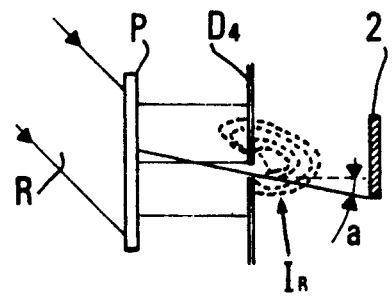
FIG. 3 diagrammatically shows a variant of the previous embodiment where the optical system is interposed between a turned over hologram and the measuring instrument.

According to the variant of FIG. 3, the optical system consists of a narrow diaphragm D4 interposed on the real image Ir of the recorded hologram. In order to reconstruct this real image Ir, the sensitive plate P is turned over in the reconstructing light beam R. The measuring instrument 2 is placed behind diaphragm D4.

Figure 4:
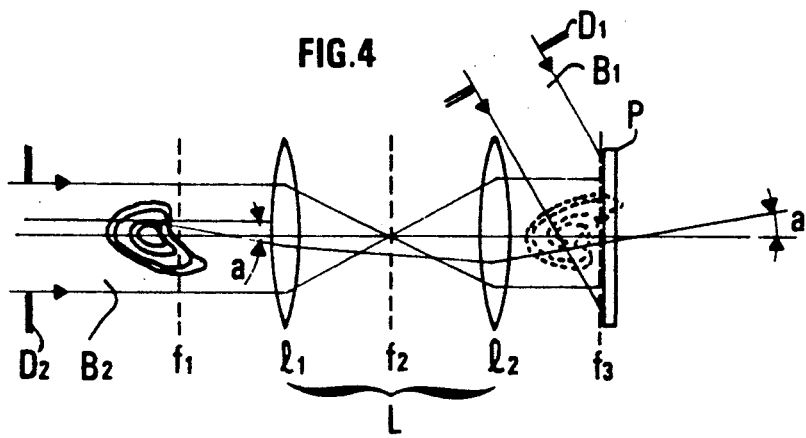
FIG. 4 diagrammatically shows a second embodiment where the light coming from the object traverses an optical system before the forming of the holograms.
Figure 5:
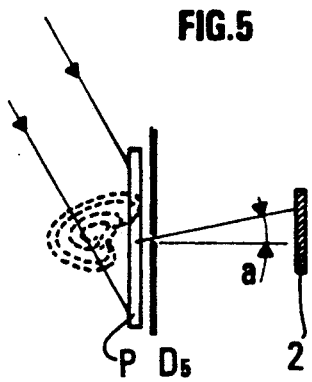
FIG. 5 diagrammatically shows a first method for measuring the image reconstructed from the hologram obtained with the second embodiment.
Figure 6:
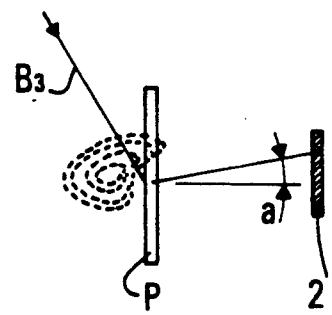
FIG. 6 very diagrammatically shows a narrow-beam variant of the previous measuring method.

According to the second embodiment of FIG. 4, the optical system is utilized at the stage of recording of the holograms. To this effect, the object to be holographed 1 is placed in the object plane of an optical system L comprising for example two lenses l1, l2. The beam traversing the object passes into the optical system L and interferes with the reference beam. A sensitive plate P (or a camera) allows fixing of each obtained hologram. During the reconstruction phase, the hologram can be optically traversed by the measuring instrument 2 through a thin aperture in a diaphragm D5 (FIG. 5). The hologram can also be directly reconstructed without a diaphragm, by means of a very thin light beam B3 (FIG. 6). This embodiment procedure is preferable when a little sensitive measuring instrument 2 is utilized.

Figure 1:
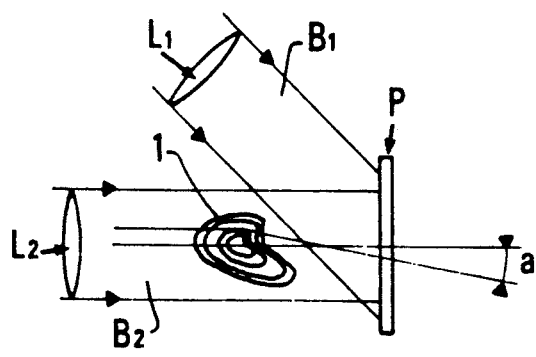
FIG. 1 diagrammatically shows the principle of the forming of the hologram of an object traversed by coherent light.

If it is known that the object 1 is not likely to cause a crossing of rays before the forming of the hologram, it is possible to record the latter as shown in FIG. 1 and to read it as shown in FIG. 5 or 6.

In the previous two embodiment procedures, the displacing of both the measuring instrument 2 and the diaphragms D3 or D4 may have drawbacks. A first solution consists in displacing only the hologram within its plane. It is then the reconstructed object which moves, and not the optical system. Another solution consists in interposing a lens with a long focal distance between diaphragm D3 or D4 and measuring instrument 2, the latter being located at the image focus of this lens. In this case, instrument 2 only measures the deflection of the rays which have traversed the diaphragm. It is not necessary to displace instrument 2 at the same time.

The embodiment procedure of FIG. 7 is suitable for all the non symmetric transparent objects because it allows reconstructing of the distribution of the values of their refraction coefficient by means of a multiplicity of beams. To this effect, a grating G interposed on the path of beam B2 divides the latter into a certain number of beams which are made to interfere with reference beams B. The holograms H1, H2 . . . formed thereby are recorded on several plates P1, P2 . . . The embodiment procedure of FIG. 2 is used for their reconstruction, for example, for each one of the beams having traversed the object. A low-pass space filter is preferably interposed and arranged in the focal plane f2 of lens L1, in order to select any one of the reconstructed beams.

I claim:

1. A holographic deflectometry process for measuring the angular deviations undergone by the light of a laser traversing an object or holograms formed from the object, said process comprising:
   (a) directing light from a laser onto an object;
   (b) passing light emanating from the object or from a hologram formed from the object through an optical system including at least two lenses, arranged in such a way that part of the reconstructed image of each obtained hologram substantially forms in the object focal plane of said optical system, and a diaphragm, substantially arranged in the image focal plane of said optical system; and
   (c) measuring the light, after passage thereof through said optical system, by receiving the light on an angular measuring instrument placed on the side of said diaphragm opposite said optical system.

2. A holographic deflectometry process for measuring the angular deviations undergone by the light of a laser traversing an object or holograms formed from the object, said process comprising:
   (a) directing light from a laser onto an object;
   (b) recording a hologram of the object on a sensitive support, turning over said sensitive support, and passing the light emanating from the hologram through a diaphragm arranged in a plane where part of the real image of the reconstituted hologram forms; and
   (c) measuring the light, after passage thereof through said optical system, by receiving the light on an angular measuring instrument place on the side of said diaphragm opposite said optical system.

3. A holographic deflectometry process for measuring the angular deviations undergone by the light of a laser traversing an object or holograms formed from the object, said process comprising:
   (a) directing light from a laser onto an object;
   (b) passing light emanating from the object or from a hologram formed from the object through an optical system including at least two lenses arranged in such a way that at least part of the examined object is in the object focal plane of said optical system and that each holographic image is substantially formed in the image focal plane of said optical system; and
   (c) measuring the light, after passage thereof through said optical system, on an angular measuring instrument.

4. A process as claimed in claim 3, wherein:
   step (b) includes recording the holographic image on a sensitive support, and
   step (c) includes receiving the light on a measuring instrument arranged on the side of said sensitive support opposite the optical system, and reconstituting the holographic image from the recording.

5. A process as claimed in claim 4, wherein:
   step (c) includes reconstituting the holographic image by means of a relatively wide light beam, and passing the reconstituted image through a diaphragm interpose between said sensitive support and said measuring instrument.

6. A process as claimed in claim 4, wherein step (c) includes reconstituting the holographic image by means of a relatively narrow light beam.

7. A holographic deflectometry process for measuring the angular deviations undergone by the light of a laser traversing an object or holograms formed from the object, said process comprising:
   (a) directing light from a laser onto an object;
   (b) passing light emanating from the object or from a hologram formed from the object through an optical system, including lighting the object with several light beams to form several holograms of the object, showing several different orientations; and
   (c) measuring the light, after passage thereof through said optical system, on an angular measuring instrument.

8. A process as claimed in claim 7, wherein step (b) includes passing the light through a space filter in the image focal plane of said optical system to measure the angular deviations of the different beams with different orientations.

9. A holographic deflectometry process for measuring the angular deviations undergone by the light of a laser traversing an object or holograms formed from the object, said process comprising:
   (a) directing light from a laser onto an object;
   (b) passing light emanating from the object or from a hologram formed from the object through an optical system; and
   (c) measuring the light, after passage thereof through said optical system, on an angular measuring instrument by measuring the angular deviations by displacing the hologram in relation to said angular measuring instrument.

10. A holographic deflectometry process for measuring the angular deviations undergone by the light of a laser traversing an object or holograms formed from the object, said process comprising:
    (a) directing light from a laser onto an object;
    (b) passing light emanating from the object or from a hologram formed from the object through an optical system; and
    (c) measuring the light, after passage thereof through said optical system, by measuring the angular deviations with an angular measuring instrument located in the image focal plane of a lens having a relatively long focal distance.

11. A holographic deflectometry device for measuring the angular deviations undergone by the light of a laser traversing an object or holograms formed from the object, said device comprising:
    optical means for forming holograms from an object;
    an optical system for receiving the light emanating from the object or from the hologram formed from the object; and an instrument for measuring the angular deviations undergone by the light rays emanating from the object after passage thereof through said optical system.

12. A holographic deflectometry device for measuring the angular deviations undergone by the light of a laser traversing an object or holograms formed from the object, said device comprising:

optical means for forming holograms from an object;

an optical system including at least two lenses and a diaphragm, for receiving the light emanating from the object or from the hologram formed from the object; and an instrument for measuring the angular deviations undergone by the light rays that have traversed the object after passage thereof through said optical system.

13. A holographic deflectometry device for measuring the angular deviations undergone by the light of a laser traversing an object or holograms formed from the object, said device comprising:

optical means for forming holograms from an object;

an optical system including at least one diaphragm for receiving the light emanating from the object or from the hologram formed from the object; and an instrument for measuring the angular deviations undergone by the light rays that have traversed the object after passage thereof through said optical system.

14. A holographic deflectometry device for measuring the angular deviations undergone by the light of a laser traversing an object or holograms formed from the object, said device comprising:

optical means for forming holograms from an object;

an optical system, including a diffraction grating for lighting up the object from several different orientations to form several different holograms of the object, and means for receiving the light emanating from the object or from the holograms formed from the object; and an instrument for measuring the angular deviations undergone by the light rays that have traversed the object after passage thereof through said optical system.

15. A holographic deflectometry process for measuring the angular deviations undergone by the light of a laser traversing an object or holograms formed from the object, said process comprising:

(a) directing light from a laser onto an object;

(b) passing light emanating from the object or from a hologram formed from the object through an optical system; and (c) measuring the light emanating from the object or from a hologram of the object, after passage thereof through said optical system, on an angular measuring instrument.

16. A holographic deflectometry process for measuring the angular deviations undergone by light traversing an object, said process comprising:

(a) positioning the object in the object focal plane of an optical system;

(b) forming on a sensitive support a hologram of the object resulting from interference between a reference light beam and a light beam traversing the object and said optical system;

(c) reconstructing an image of the hologram by selecting at least a part of the reconstructed image by means of a diaphragm; and (d) measuring light from the reconstructed image on an angular measuring instrument positioned behind said diaphragm.

17. A holographic deflectometry process for measuring the angular deviations undergone by light traversing an object, said process comprising:

(a) positioning the object in the object focal plane of an optical system;

(b) forming on a sensitive support a hologram of the object resulting from interference between a reference light beam and a light beam traversing the object and said optical system;

(c) reconstructing an image of the hologram by projecting a thin light beam to form the reconstructed image directly on said angular measuring instrument; and (d) measuring light from the reconstructed image on an angular measuring instrument.

18. A holographic deflectometry process for measuring the angular deviations undergone by light traversing an object, said process comprising:

(a) forming on a light sensitive support a hologram of an object resulting from interference between a reference light beam and a light beam traversing the object;

(b) illuminating said light sensitive support with a reconstruction beam to form a reconstructed image of the hologram in the object focal plane of an optical system; and measuring light from said optical system on an angular measuring instrument by (c) measuring light from said optical system on an angular measuring instrument by passing light from said optical system through a diaphragm positioned at the image focal plane of said optical system, and positioning said angular measuring instrument behind said diaphragm.

19. A holographic deflectometry process for measuring the angular deviations undergone by light traversing an object, said process comprising:

(a) forming on a light sensitive support a hologram of an object resulting from interference between a reference light beam and a light beam traversing the object;

(b) turning over said light sensitive support to form a real image of the hologram;

(c) selecting at least a part of the real image by means of a diaphragm; and (d) measuring light of the selected port from said diaphragm on an angular measuring instrument positioned on the side of said diaphragm opposite said light sensitive support.

20. A process as claimed in any one of claims 1, 2, 3, 4, 5, or 6, wherein step (b) includes lighting the object with several light beams to form several holograms of the object, showing several different orientations.

* * * * *